(12) United States Patent
Kim et al.

(10) Patent No.: US 12,290,540 B2
(45) Date of Patent: May 6, 2025

(54) STRAIN HAVING ABILITY TO LOWER BLOOD AMMONIA LEVELS AND COMPOSITION COMPRISING SAME FOR NEURONAL PROTECTION

(71) Applicant: JINIS CO., LTD, Jeollabuk-do (KR)

(72) Inventors: Hyeon Jin Kim, Jeollabuk-do (KR); Sang Woo Kim, Iksan-si (KR); Seong Tshool Hong, Jeonju-si (KR)

(73) Assignee: JINIS CO., LTD, Jeollabuk-do (KR)

( * ) Notice: Subject to any disclaimer, the term of this patent is extended or adjusted under 35 U.S.C. 154(b) by 551 days.

(21) Appl. No.: 17/638,528

(22) PCT Filed: Nov. 19, 2020

(86) PCT No.: PCT/KR2020/016352
§ 371 (c)(1),
(2) Date: Mar. 8, 2022

(87) PCT Pub. No.: WO2021/107500
PCT Pub. Date: Jun. 3, 2021

(65) Prior Publication Data
US 2022/0409678 A1      Dec. 29, 2022

(30) Foreign Application Priority Data

Nov. 29, 2019   (KR) .................. 10-2019-0156386
Aug. 4, 2020    (KR) .................. 10-2020-0097141

(51) Int. Cl.
| | | |
|---|---|---|
| A61K 39/02 | (2006.01) | |
| A61K 35/744 | (2015.01) | |
| A61K 35/747 | (2015.01) | |
| A61K 39/09 | (2006.01) | |
| A61P 25/28 | (2006.01) | |
| C12N 1/00 | (2006.01) | |
| C12N 1/20 | (2006.01) | |

(52) U.S. Cl.
CPC .......... *A61K 35/747* (2013.01); *A61K 35/744* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 9,487,764 B2 | 11/2016 | Falb et al. | |
| 9,688,967 B2 | 6/2017 | Falb et al. | |
| 11,135,181 B2 * | 10/2021 | Vitetta | A23L 33/135 |
| 11,273,188 B2 | 3/2022 | Kim et al. | |
| 2018/0369129 A1 | 12/2018 | Weiss et al. | |
| 2019/0105359 A1 | 4/2019 | Bushman et al. | |
| 2021/0196767 A1 | 7/2021 | Minami et al. | |

FOREIGN PATENT DOCUMENTS

| | | |
|---|---|---|
| EP | 3375448 A1 | 9/2018 |
| JP | 2009-102324 A | 5/2009 |
| KR | 1020160098955 A | 8/2016 |
| WO | 2016/090343 A1 | 6/2016 |
| WO | 2016/200614 A2 | 12/2016 |
| WO | 2019189408 A1 | 10/2019 |

OTHER PUBLICATIONS

Akbari et al (Front Aging Neurosci. vol. 8. Article 256. Nov. 10, 2016, pp. 1-8).*
Luo et al (Sci China Life Sci. Mar. 2014;57(3):327-335).*
Liu et al (Frontiers in Cellular and Infect. Microbio. Jan. 2022 (after priority date) vol. 11. Article 696044. pp. 1-11).*
Hea-Jong Chung et al. "Intestinal removal of free fatty acids from hosts by Lactobacilli for the treatment of obesity", FEBS openbio 6, 2016, pp. 64-676.
Lin Jia et al. "Comparison of probiotics and lactulose in the treatment of minimal hepatic encephalopathy in rats" World J. Gastroenterol. 2005, 11(6), pp. 908-911.
Singh, Parul et al., "Elucidation of the anti-hyperammonemic mechanism of Lactobacillus amylovorus JBD401 by comparative genomic analysis", BMC Genomics, 2018, vol. 18, Article 292, pp. 1-14.
Singh, Parul, "Elucidation of the anti-hyperammonemic mechanism of Lactobacillus amylovorus JBD401 by comparative genomic analysis", Dissertation submitted to Chonbuk National University, Jeonju, South Korea, Aug. 22, 2018, 1-94.
Jing Liu et al., "The pharmabiotic approach to treat Hyperammonemia", Nutrients 2018, vol. 10, Article 140, pp. 1-18, Jan. 28, 2018.
Yan Yan Jin et al., "Blood ammonia as a possible etiological agent for alzheimer's disease", Nutrients, vol. 10, Article 564, pp. 1-13, May 4, 2018.

* cited by examiner

*Primary Examiner* — Jennifer E Graser
(74) *Attorney, Agent, or Firm* — NKL Law; Jae Youn Kim

(57) ABSTRACT

Microorganisms for lowering blood ammonia level and composition for protecting neuronal cells containing the same, particularly relates to microbes or a symbiotic pair that has a neuroprotective function by lowering blood ammonia levels or reducing ammonia levels in the body and composition for protecting neuronal cells comprising the microbes. The microorganisms having a neuroprotective function by lowering the blood ammonia level can be selected from the group that include, but not limited to, a *Lactobacillus* sp. strain and a *Streptococcus* sp. strain. The ammonia removal strains and the composition have a neuroprotective effect by their excellent ability to remove neurotoxic ammonia, and thus can be widely used as a preventive or therapeutic agent for hyperammonemia and neurological diseases caused thereby.

3 Claims, 5 Drawing Sheets
Specification includes a Sequence Listing.

serum stomach intestine colon feces urine

STRAIN HAVING ABILITY TO LOWER BLOOD AMMONIA LEVELS AND COMPOSITION COMPRISING SAME FOR NEURONAL PROTECTION

INCORPORATION OF SEQUENCE LISTING

This application contains a sequence listing in Computer Readable Form (CRF). The CRF file containing the sequence listing entitled "1-4-PK3805290-SeqListing.txt", which was created on Mar. 3, 2022, and modified on Mar. 8, 2022, and is 806 bytes in size. The information in the sequence listing is incorporated herein by reference in entirety.

TECHNICAL FIELD

The present application relates to novel microorganisms for lowering blood ammonia level and composition for protecting neuronal cells containing the same, particularly relates to microbes or a symbiotic pair that has a neuroprotective function by lowering blood ammonia levels or reducing ammonia levels in the body and composition for protecting neuronal cells comprising the said microbes.

BACKGROUND ART

In our body, the metabolism of protein ingested through food constantly occurs, and ammonia is produced in the process of protein digestion. Ammonia is a very potent neurotoxic compound and thus it is rapidly converted to urea in the liver through the urea cycle for its excretion in the urine. However, when the level of ammonia in the body is abnormally high due to defects in liver function, the neurotoxic ammonia can acts as a causative agent for various neurological diseases such as dementia, Parkinson's disease, stroke, coma, and an encephalopathy that might cause a sudden loss of consciousness and death.

To date, various methods for removing ammonia from the body have been developed, including hemodialysis, plasma removal, bowel washing, etc. Since these treatments for ammonia removal are not effective, they have been mostly used to relieve symptoms in an emergency situation when the ammonia level in the body is very high. In addition, current agents, non-absorbable sugars such as lactulose, lactitol, and xylobiose, non-absorbable antibiotics such as neomycin, paromycin, and rifaximin, and ammonia-excreting agents such as arginine, sodium benzoate, and sodium phenylacetate, have been used with little efficacy but severe side effects. Recently, technologies for alleviating hyperammonemia using genetically modified microorganism strains have been developed (WO/2016/090343, WO/2016/200614. U.S. Pat. Nos. 9,487,764, 9,688,967). Unfortunately, those strains cannot be transplanted to the intestine to lower ammonia levels in the body, demanding the development of a technology for removing blood ammonia efficiently.

The intestine is the site where the digested nutrients in the intestinal lumen are absorbed through intestinal capillaries and lymphatic vessels. Unlike nutrients, metabolites flow bi-directionally, traveling from the intestinal lumen to the intestinal capillaries/lymphatic ducts or from the intestinal capillaries/lymphatic ducts to the intestinal lumen. Among the metabolites that can move in both directions, ammonia is the one for which excretion is particularly important. The critical organ for ammonia transport is the intestine where ammonia is absorbed from the intestinal lumen into the intestinal capillaries/lymphatic ducts through passive diffusion and specific transporters such as RhBG. When ammonia levels in the intestinal lumen become low, blood ammonia moves from the intestinal capillaries/lymphatic ducts into the intestinal lumen by chemical equilibrium.

Ammonia is a neurotoxic compound that is inevitably produced as a by-product of amino acid metabolism in the body. The increased level of blood ammonia can cause various neurological diseases. The effective treatment that can lower ammonia levels in the blood has yet to be developed.

Current treatments such as non-absorbable sugars, non-absorbable antibiotics, and substances that promote ammonia excretion are not effective while its side effects are significant. Attempts to develop a therapeutic agent for lowering blood ammonia levels using genetically engineered microorganisms have not been successful due to the following reasons; ① it is very limited in efficacy to remove ammonia surrounding the microorganisms by administration of single microbial species; ② it has been difficult for single microbial species to be successfully transplanted to the intestines.

Therefore, as a result of efforts to solve the above problems, the researchers successfully demonstrated that a set of intestinal strains in a positive-interacting symbiotic relationship, also called a symbiotic pair, could promote mutual growth of each other strains, could be transplanted to the intestine successfully, and thus eventually could remove surrounding ammonia effectively, and thereby completed this invention.

DISCLOSURE OF INVENTION

Technical Problem

One object of this invention is to provide a single microbial species or a symbiotic pair having neuroprotective efficacy by lowering blood ammonia levels or reducing ammonia levels in the body and to provide a composition for protecting neuronal cells comprising the said microbes.

Another object of the present invention is to provide as an active ingredient a single species microbe having neuroprotective activity by reducing the level of ammonia in the blood, a symbiotic partner thereof, a symbiotic pair thereof, any combination of said microbes, or a culture thereof, to prevent or treat hyperammonemia and neurological diseases resulting therefrom.

Technical Solution

To accomplish the said objects, the present invention provides novel microbes having neuroprotective efficacy by lowering blood ammonia levels in mammals, and said microbial species can be selected from *Lactobacillus* species. In this invention, said *Lactobacillus* species can be selected from the groups that include, but are not limited to, *L. reuteri* JBD301 (KCTC 12606BP), *L reuteri* JBD400 (KACC 81122BP), *L. amylovorus* JBD401 (KACC 81052BP), *L. plantarum* JBD402 (KACC 81121BP), *L. rhamnosus* JBD406 (KACC 81123BP), *L. acidophilus* JBD410 (KCTC 11515BP), and *L. coryniformis* JBD411 (KACC 81053BP). Under the provisions of the Budapest Treaty on the International Recognition of the Deposit of Microorganisms for the Purposes of Patent Procedure, novel strains of *Lactobacillus* species were deposited with the international depositary authority: the Biological Resources Center in the Korean Agricultural Culture Collection (KACC) on Jul. 7, 2020. *Lactobacillus reuteri* JBD400 was under the accession number KACC 81122BP, *Lactobacillus plantarum* JBD402 was under the accession number KACC 81121BP, *Lactobacillus rhamnosus* JBD406 was under the accession number KACC 81123BP, and *S. lubneri* JBD420 was under the accession number KACC 81124BP.

The present invention also provides novel microbes having neuroprotective efficacy by lowering blood ammonia levels in mammals, and said microbial species can be selected from *Streptococcus* species. In this invention, said *Streptococcus* species can be selected from the groups that include, but are not limited to, *S. lubneri* JBD420 (KACC 81124BP), *S. lutetiensis* JBD421 (KACC 81054BP), *S. australis* JBD422 (KACC 81055BP), *S. mutans* JBD423 (KACC 81056BP), *S. vestibularis* JBD424 (KACC 81057BP), *S. sanguinis* JBD425 (KACC 81058BP), *S. parasanguinis* JBD426 (KACC 81059BP), *S. gallinaceus* JBD427 (KACC 81060BP), Under the provisions of the Budapest Treaty on the International Recognition of the Deposit of Microorganisms for the Purposes of Patent Procedure, novel strains of *Streptococcus* species were deposited with the international depositary authority: the Biological Resources Center in the Korean Agricultural Culture Collection (KACC) on Nov. 30, 2017. *S. lutetiensis* JBD421 strain was under the accession number KACC 81054BP), *S. australis* JBD422 strain was under the accession number KACC 81055BP), *S. mutans* JBD423 strain was under the accession number KACC 81056BP), *S. vestibularis* JBD424 strain was under the accession number KACC 81057BP), *S. sanguinis* JBD425 strain was under the accession number KACC 81058BP), *S. parasanguinis* JBD426 strain was under the accession number KACC 81059BP), and *S. gallinaceus* JBD427 strain was under the accession number KACC 81060BP.

The present invention also provides a composition comprising one or more active ingredients that can be selected from the groups that include a *Lactobacillus* sp. strain lowering a blood ammonia level, a *Streptococcus* sp. strain lowering a blood ammonia level, or cultures of the strains selected from the group.

In the present invention, the composition for protecting nerve cells is characterized in that it has the ability to prevent or treat hyperammonemia and neurological diseases due to it.

Benefits

The strain and composition according to the present invention have neuroprotective efficacy based on its removal capacity of neurotoxic ammonia.

DETAILED DESCRIPTION OF PREFERRED EMBODIMENTS

Figure 1:
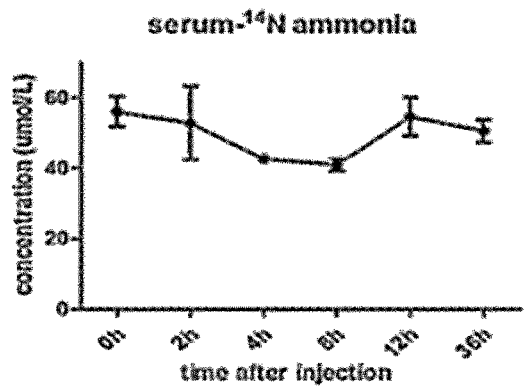
FIG. 1 and FIG. 2 present the ammonia levels, $^{14}NH_4$ and $^{15}NH_4$, measured by LC-MS/MS using the samples of blood, stomach, small intestine, large intestine, urine, and feces at each indicated times after intravenous administration of the radiolabeled ammonia to the mice according to Example 1.
Figure 1:
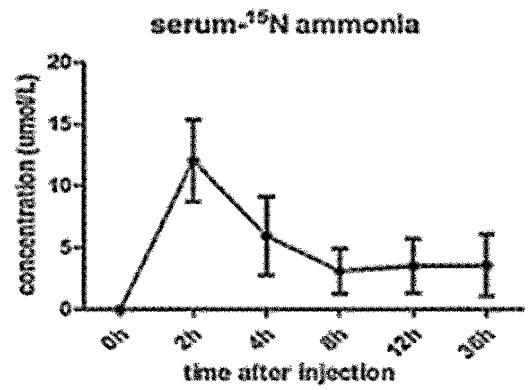
Figure 1:
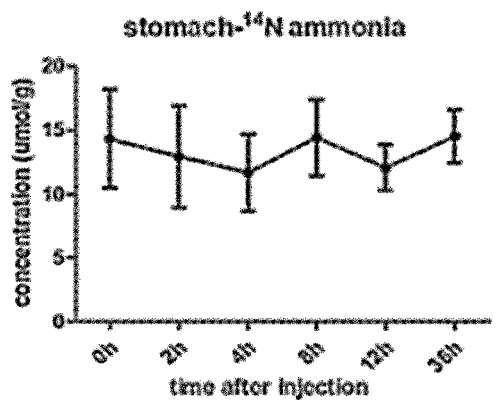
Figure 1:
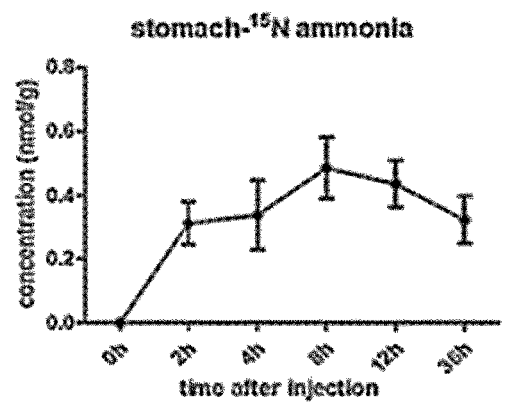
Figure 1:
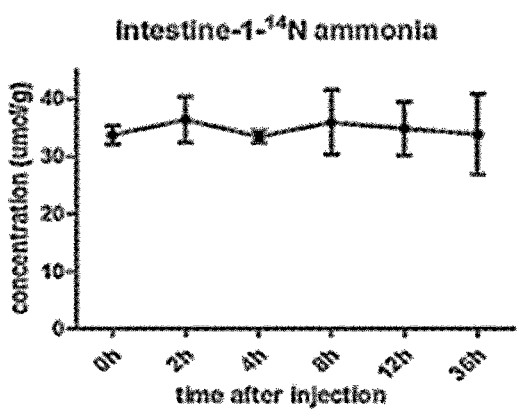
Figure 1:
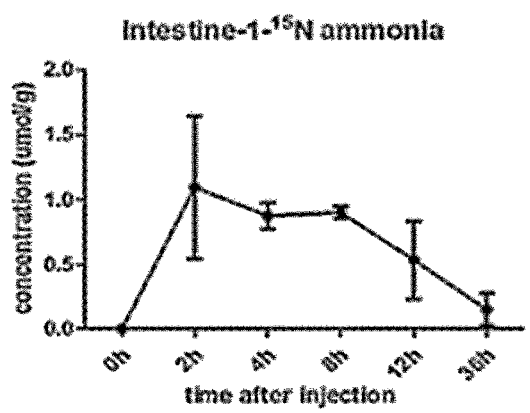

It has been difficult to effectively treat neurological diseases resulting from the accumulation of neurotoxic ammonia in the body by current physical hemodialysis method or drugs that inhibit ammonia absorption. Moreover, it is not possible for these treatments to prevent or regulate the level of neurotoxic ammonia in the body before the onset of the disease.

In this invention, the inventors recognized the limitations of current ammonia removal technology and the possibility of treatment or prevention of neurological diseases by reducing ammonia levels in the body using intestinal microorganisms having excellent ability to remove ammonia. Ammonia is a neurotoxic compound that is inevitably produced as a by-product of the metabolism of nitrogenous compounds in the body. It is absorbed from the intestinal lumen into intestinal capillaries/lymph ducts, and then converted to urea in the liver and excreted in the urine. Unlike nutrients, ammonia can flow bi-directionally, traveling from the intestinal lumen to the intestinal capillaries/lymphatic ducts or from the intestinal capillaries/lymphatic ducts to the intestinal lumen.

Therefore, in this invention, attention was paid to the fact that lowering the concentration of ammonia in the intestinal lumen could facilitate the transport of the ammonia in the body to the intestinal lumen by chemical equilibrium, lowering the level of ammonia in the body. Therefore, it was attempted to confirm that the ingestion of intestinal ammonia-removal microorganisms can prevent or treat neurological diseases by lowering the ammonia levels in the body.

In this invention, it was also attempted to confirm that ammonia removal ability can be further enhanced with a combination of symbiotic pair strains having a mutual growth-promoting effect as well as ammonia removal ability. Since microorganisms are unicellular organisms, their genes are very small compared to multicellular organisms. In fact, the average genome size of each bacterium is only $\frac{1}{1,000}$ that of mammals. Due to their limited ability to adapt to the surrounding environment with their own genome, most microorganisms prefer symbiotic coexistence with each other. Based on this understanding, the present inventors first carried out a high throughput screening of human intestinal microbes to discover candidate strains with excellent ammonia removal capability. After the discovery of ammonia-removal microbes, additional high throughput screening of human intestinal microbes was carried out to identify its symbiotic partner. The resulting symbiotic pair was administered, confirming that a specific set of symbiotic pair, *Lactobacillus* sp. and *Streptococcus* sp., could have remarkably excellent ammonia removal capability.

In this invention, we confirmed that (1) the ammonia removal microbes and their symbiotic partner microbes having mutual growth-promoting effects with them were identified by in vitro screening of intestinal microorganisms; (2) a specific set of symbiotic pair, *Lactobacillus* sp. and *Streptococcus* sp., with ammonia removal capability, remarkably reduced the ammonia level in the body of a host; and (3) a symbiotic pair for ammonia removal had a preventive and therapeutic effect on hyperammonemia and neurological diseases by lowering blood ammonia and protecting host neuronal cells.

Therefore, in the first aspect, this invention relates to the microbes having a neuroprotective efficacy by lowering ammonia concentrations in the body of a mammal.

In this invention, said microbes having the neuroprotective ability can be any microbes derived from the gut of a mammal having the neuroprotective ability by reducing the ammonia concentration in the body without any limitation. Preferably, said gut microbes can be selected from the groups that include, but are not limited to, *Lactobacillus* species, *Streptococcus* species, or a symbiotic pair.

In this invention, said *Lactobacillus* species can be selected from the groups that include, but are not limited to, *L. coryniformis, L. acidophilus, L. amylovorus, L. reuteri, L. plantarum*, and *L. rhamnosus*, and said *Streptococcus* species can be selected from the groups that include, but are not limited to, *S. lubneri, S. lutetiensis, S. australis, S. mutans, S. vestibularis, S. sanguinis, S. parasanguinis*, and *S. gallinaceus*.

In a preferred embodiment of the invention, said *Lactobacillus* sp. can be selected from the groups that include, but are not limited to, *L. reuteri* JBD301 (KCTC 12606BP), *L. reuteri* JBD400 (KACC 81122BP), *L. amylovorus* JBD401 (KACC 81052BP), *L. plantarum* JBD402 (KACC 81121BP), *L. rhamnosus* JBD406 (KACC 81123BP), *L. acidophilus* JBD410 (KCTC 11515BP), and *L. coryniformis* JBD411 (KACC 81053BP) strains and said *Streptococcus* sp. can be selected from the groups that include, but are not limited to, *S. lubneri* JBD420 (KACC 81124BP), *S. lutetiensis* JBD421 (KACC 81054BP), *S. australis* JBD422 (KACC 81055BP), *Streptococcus mutans* JBD423 (KACC 81056BP), *S. vestibularis* JBD424 (ACC 81056BP), *S. vestibularis* JBD424 (KACC 81056BP), *S. sanguinis* JBD425 (KACC 81058BP), *S. parasanguinis* JBD426 (KACC 81059BP), and *S. gallinaceus* JBD427 (KACC 81060BP).

Preferably, said neuroprotective microbes are pharmabiotic strains with the following 4 advantageous characteristics compared to the current neuroprotective compositions.

First, it is a naturally effective intestinal microbe with inherent safety without any side effects, unlike chemical-based treatments. Second, the long-term safety of the intestinal microbes is outstanding without any concern about side effects since intestinal microbes act in the intestinal lumen without being absorbed into our body while conventional drugs need to be absorbed and metabolized in the body, resulting in side effects. Third, pharmabiotic treatment is convenient and effective compared to dialysis and intestinal lavage. Fourth, ammonia, a neurotoxic compound constantly generated in the body, can be safely removed by pharmabiotic administration, thereby protecting neurons and preventing neurological diseases and diseases related to the nervous system.

The said neurological diseases and diseases related to the nervous system can include, but are not limited to, hyperammonemia, cerebral toxicity, neurotoxicity, nerve damage, respiratory alkalemia, coma, vomiting, seizures, liver disease, brain developmental disorder, mental retardation, stunting, and encephalopathy.

In another aspect, the present invention relates to compositions that contain as an active ingredient a microbe or culture that can be selected from the groups that include, but are not limited to, *Lactobacillus* species that can lower blood ammonia levels, *Streptococcus* species that can lower blood ammonia levels, or culture thereof.

Preferably, said *Lactobacillus/Streptococcus* is a symbiotic pair having a mutual growth-promoting symbiotic effect.

In a preferred embodiment of the invention, said composition contains *Lactobacillus* sp. that can be selected from the groups that include, but are not limited to, *L. reuteri* JBD301 (KCTC 12606BP), *L. reuteri* JBD400 (KACC 81122BP), *L. amylovorus* JBD401 (KACC 81052BP), *L. plantarum* JBD402 (KACC 81121BP), *L. rhamnosus* JBD406 (KACC 81123BP), *L. acidophilus* JBD410 (KCTC 11515BP), and *L. coryniformis* JBD411 (KACC 81053BP) strains and *Streptococcus* sp. that can be selected from the groups that include, but are not limited to, *S. lubneri* JBD420 (KACC 81124BP), *S. lutetiensis* JBD421 (KACC 81054BP), *S. australis* JBD422 (KACC 81055BP), *Streptococcus mutans* JBD423 (KACC 81056BP), *S. vestibularis* JBD424 (ACC 81056BP), *S. vestibularis* JBD424 (KACC 81056BP), *S. sanguinis* JBD425 (KACC 81058BP), *S. parasanguinis* JBD426 (KACC 81059BP), and *S. gallinaceus* JBD427 (KACC 81060BP).

In another aspect, the present invention relates to pharmaceutical compositions or a functional food composition containing a gut microbe or culture with neuroprotective efficacy.

In another aspect, said pharmaceutical compositions or functional food compositions as microbes or the cultures can lower the ammonia concentration in the body, up to 90% removal of blood ammonia, and said body may include blood, stomach, small intestine, large intestine, and brain.

Preferably, said microbes or cultures may be contained, but not restricted, at a dose of $10^3 \sim 10^{12}$ cfu/gram in pharmaceutical or functional food compositions.

In this invention, said pharmaceutical compositions could be formulated, but not limited to, with more than 1 kind of pharmaceutically acceptable carrier in addition to said microbes or cultures having a neuroprotective efficacy by lowering ammonia concentrations in the blood.

In this invention, said functional foods are foods supplemented with functional ingredients and include, but not limited to, health food, nutraceuticals, dietary supplement, pharmabiotics. Preferably, said functional ingredients is for neuroprotection.

Said functional foods include, but not limited to, dairy food (milk, soy milk, processed milk), fermented milk (drinking yogurt, set curd yogurt), drink, and soda, Said functional foods can include various supplementary components in addition to the functional ingredients. In addition, said functional foods of the present invention may contain various flavors or natural carbohydrates as additional components as in the case of ordinary beverages.

Said pharmaceuticals and functional foods in this invention contain said microbes having a neuroprotective efficacy, and thus the administration of said pharmaceuticals and functional foods reduce the ammonia levels in the body, thereby having a neuroprotective function and contributing to the prevention and/or treatment of a neurological disease.

The technical idea of the present invention can be applied to any microbes with a neuroprotective efficacy by lowering ammonia concentrations in the host body when ingested by a mammal, and will be apparent to those skilled in the art to which the present invention pertains.

EXAMPLES

The present invention may be better understood with reference to the accompanying examples that are intended for purposes of illustration only and should not be construed to limit the scope of the invention, as defined by the claims appended hereto.

Experiment 1. An Experiment to Determine if Blood Ammonia Levels can be Reduced by Excretion of Ammonia Through the Intestinal Lumen to the Outside of the Body While digested nutrients move uni-directionally from the intestinal lumen to the intestine through capillaries and lymphatic vessels, human metabolites move bi-directionally from the intestinal lumen to the intestinal capillaries/lymphatic ducts or from the intestinal capillaries/lymphatic ducts to the intestinal lumen, i.e. in both directions. In particular, the present inventors hypothesized that ammonia, a metabolic by-product, can move between the intestinal lumen and intestinal capillaries/lymphatic ducts by passive diffusion since ammonia is both hydrophilic and hydrophobic. Thus, if ammonia levels in the intestinal lumen become low, blood ammonia moves from the intestinal capillaries/lymphatic ducts into the intestinal lumen by chemical equilibrium, eventually lowering blood ammonia levels.

Figure 2:
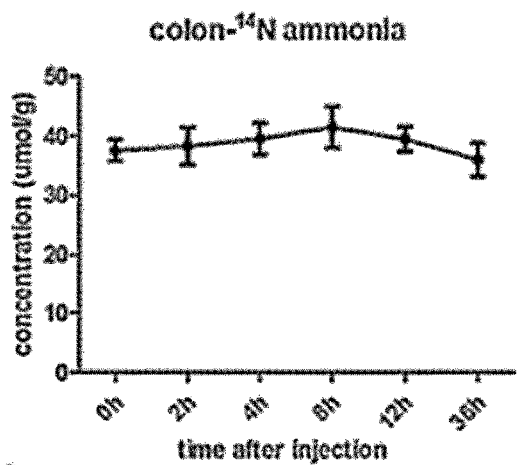
Figure 2:
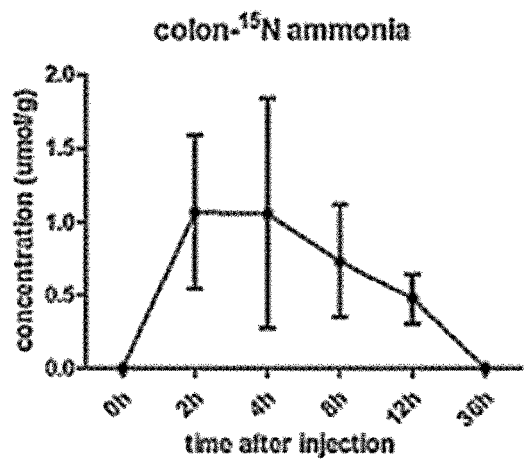
Figure 2:
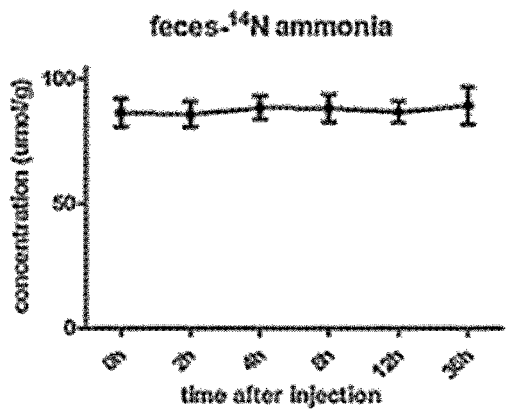
Figure 2:
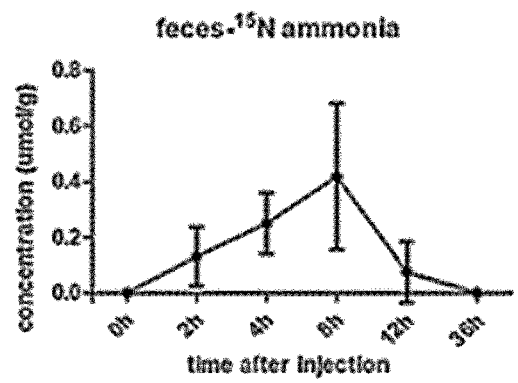
Figure 2:
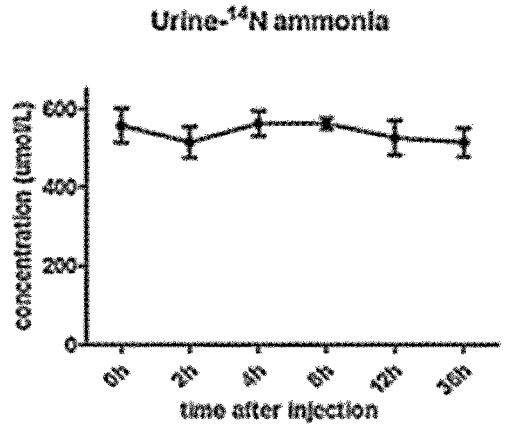
Figure 2:
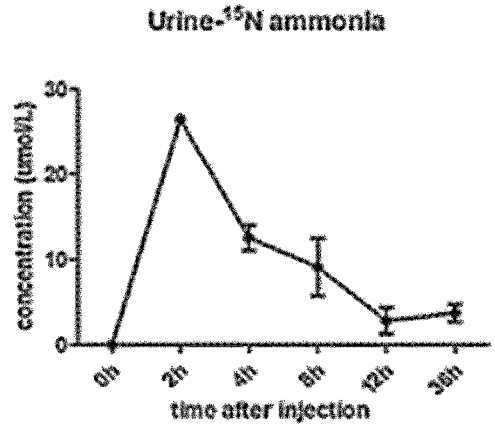

Accordingly, the present inventors confirmed if ammonia in the blood can actually moves into the intestine and is excreted outside the body using animals upon injection of ammonia labeled with a radioactive isotope into the blood, First, 10 mg/mL $^{15}NH_4Cl$ in 0.9% physiological saline was prepared and intravenously injected into the tail of each mouse at a dose of 250 mg/kg of body weight. After indicated period of time, samples were collected from the blood, stomach, small intestine, large intestine, urine, and feces followed by quantitation of ammonia ($^{14}NH$ and $^{15}NH_4$) present in each sample by LC-MS/MS. (FIG. 1 and FIG. 2)

The above experiment demonstrated that the radiolabelled ammonia, $^{15}NH_4$, in the blood by intravenous injection was excreted in feces and urine after transport from the blood to the digestive system. This experimental result proves that if ammonia is removed in the intestinal lumen, part of the digestive system, blood ammonia moves to the intestinal lumen, lowering blood ammonia level.

Experiment 2. Discovery of Intestinal Microbes in a Symbiotic Relationship with Ammonia Removal Lactobacillus sp.

Lactobacillus is a representative lactic acid bacteria ingested by humans and has various functions beneficial to human health. One of them is the ability to remove ammonia. In general, however, the efficacy of Lactobacillus strains to lower blood ammonia is very limited, not enough to be used for the purpose of lowering blood ammonia levels. To overcome this problem, the present inventors intended to identify a Lactobacillus strain with strong efficacy of ammonia removal as well as its symbiotic partner strains in order to explore the possibility of effectively lowering the ammonia levels of blood and brain by a symbiotic pair of Lactobacillus and its symbiotic partner.

Accordingly, the present inventors conducted an experiment of co-culturing various species of intestinal microbes from Gut Microbiota Bank (www.gutmicrobiotabank.com) with various Lactobacillus strains. The present inventors incubated L. acidophilus in MRS media anaerobically at 37° C. for 24 hours, and then diluted 0.1 $OD_{600}$ with fresh MRS media. After dispensing 150 μL of diluted L. acidophilus culture into each well of a 96-well plate, 10 μL of a 24-hour culture of various intestinal microorganisms was added to each well. After incubating the mixed culture at 37° C. anaerobically for 2 hours, $OD_{600}$ was measured to determine the growth of L. acidophilus affected by co-culture with each intestinal microorganism. The present inventors measured the growth rates of L. acidophilus co-cultured with each of 307 species of intestinal microorganisms, and Table 1 shows only a part of the experimental data obtained. The experimental results well indicated that microorganisms belonging to the genus Streptomyces have a symbiotic relationship with L. acidophilus. Experiments described in Table 1 were also performed with various species of Lactobacillus genus, namely L. amylovorus, L. casei, L. paracasei, L. fermentum, L. plantarum, L. reuteri, L. crispatus, L. gallinarum, L. ultunensis, L. intestinalis, L. kalixensis, L. jensenii, L. delbruecki, L. bulgaricus, L. iners, L. johnsonii, L. gasseri, L. gastricus, L. vaginalis, L. oris, L. antri, L. amylophilus, L. bifermentans, L. dextrinicus, L. farciminis, L. alimentarius, L. collinoides, L. brevis, L. parabuchneri, L. kefiri, L. buchneri, L. lindneri, L. fructivorans, L. sakei, L. graminis, L. coryniformis, Pediococcus acidilactici, L. pantheri, L. rhamnosus, L. zeae, L. casei, L. mali, L. saerimneri, L. salivarius, L. agilis, and L. ruminis. The best growth of Lactobacillus were all obtained from the co-culture with Streptococcus sp. as indicated in Table 1 (marked with *). From co-culture experiments, the inventors confirmed the symbiotic relationship between Lactobacillus and Streptococcus.

TABLE 1

| Intestinal microorganisms co-cultured with L. acidophilus JBD410 | $OD_{600}$ measurements |
|---|---|
| Collinsella stercoris | 0.46 ± 0.06 |
| Enorma massiliensis | 0.38 ± 0.07 |
| Actinomyces israelii | 0.35 ± 0.12 |
| Mobiluncus mulieris | 0.38 ± 0.09 |
| Bifidobacterium scardovii | 0.33 ± 0.05 |
| Bifidobacterium longum | 0.37 ± 0.02 |
| Staphylococcus capitis | 0.38 ± 0.05 |
| Staphylococcus cohnii | 0.42 ± 0.04 |
| Bacillus cereus, Bacillus | 0.44 ± 0.07 |
| Clostridium clostridioforme | 0.34 ± 0.05 |
| * Streptococcus downei | 0.71 ± 0.09* |
| * Streptococcus constellatus | 0.45 ± 0.11* |
| * Streptococcus sanguinis | 0.51 ± 0.10* |
| * Streptococcus ratti | 0.63 ± 0.13* |
| * Streptococcus thermophilus | 0.87 ± 0.15* |
| * Streptococcus sanguis | 0.64 ± 0.11* |
| * Streptococcus sobrinus | 0.56 ± 0.12* |
| Clostiridium oroticum | 0.37 ± 0.09 |
| Coprobacillus catenaformis | 0.39 ± 0.04 |
| Anaerococcus vaginalis | 0.35 ± 0.06 |
| Anaerococcus tetradius | 0.42 ± 0.08 |
| Alistipes finegoldii | 0.37 ± 0.05 |
| Porphyromonas somerae | 0.38 ± 0.08 |
| Prevotella nigrescens | 0.39 ± 0.02 |

TABLE 1-continued

| Intestinal microorganisms co-cultured with L. acidophilus JBD410 | OD$_{600}$ measurements |
|---|---|
| Ewingella americana | 0.34 ± 0.03 |
| Aeromonas enteropelogenes | 0.41 ± 0.05 |
| Campylobacter rectus | 0.39 ± 0.04 |

Experiment 3. Screening of Lactobacillus and Streptococcus strains with excellent Ammonia Removal Ability In order to discover a symbiotic pair for outstanding efficacy of neuroprotection, a screening experiment was performed as described. In vitro ammonia removal ability was screened for the Lactobacillus genus and Streptococcus genus from the human intestinal microbial libraries in JINIS Co and Gut Microbiota Bank (www.gutmicrobiotabank.com). Briefly, 250 μl of MRS broth was placed in a 96-well plate for the fresh culture of the testing microbial strain. The obtained fresh culture was inoculated onto MRS agar, followed by the anaerobic culture at 37° C. for 48 hours. The colonies grown on MRS agar were inoculated into MRS broth and then anaerobically cultured at 37° C. Finally, 500 μl of the culture with an OD$_{600}$ value of 0.45 to 1 was transferred to an Eppendorf tube and then 10 μl of ammonium hydroxide (30 μg/mL) was added. After 30 min incubation at 37° C., the reaction was centrifuged at 7,000 rpm for 5 minutes at 4° C. The supernatant was collected and the amount of ammonia in the supernatant was calculated after measuring the absorbance of the colorimetric reaction with Ammonia Assay Kit AA0100 (Sigma-Aldrich). From the experimental results with Lactobacillus and Streptococcus strains, S. lubneri JBD420, S. lutetiensis JBD421, S. australis JBD422, S. mutans JBD423, S. vestibularis JBD424, S. sanguinis JBD425, S. parasanguinis JBD426, S. gallinaceus JBD427, L. reuteri JBD301, L. reuteri JBD400, L. amylovorus JBD401, L. plantarum JBD402, L rhamnosus JBD406, L. acidophilus JBD410, and L. coryniformis JBD411 were discovered as the best ammonia-removing strains.

Example 1: Development of 'Ammonia-Lowering Pharmabiotic Drug' with the Amplified Capability of Ammonia Removal Using a Symbiotic Relationship Next, in order to discover the best symbiotic pair for outstanding efficacy of neuroprotection, we performed repeated ammonia removal assays as described with individual strains or various sets of symbiotic pairs using the identified microbes with excellent efficacy of ammonia removal from Experiment 2 and Experiment 3 in this invention. Briefly, Streptococcus strains or Lactobacillus strains were grown on MRS agar, and inoculated into MRS broth for anaerobic co-culture at 37° C. When the OD$_{600}$ value was between 0.45 and 1, 10 μl of ammonium hydroxide (30 μg/mL) was added to 250 μl of the culture using Streptococcus sp., and Lactobacillus sp. After anaerobic incubation for 30 minutes at 37° C., the supernatant was obtained by centrifugation at 4° C. for 5 minutes at 7,000 rpm. The amount of ammonia was calculated after measuring the absorbance with Ammonia Assay Kit AA0100 (Sigma-Aldrich). A blank MRS medium without the inoculation of microbes was used as a control group. The ammonia concentration of each test group and percent of the controls are shown in Tables 2, 3, 4 and 5.

TABLE 2

|  | ammonia conc. (mM) | % of control |
|---|---|---|
| control MRS | 103.6 | 100 |
| JBD411 | 28.6 | 27.61 |
| JBD421 | 29.7 | 28.67 |
| JBD411 + JBD421* | 3.3 | 3.19 |
| JBD422 | 36.4 | 35.14 |
| JBD411 + JBD422 | 9.5 | 9.17 |
| JBD423 | 22.3 | 21.53 |
| JBD411 + JBD423 | 92.6 | 89.38 |
| JBD424 | 84.1 | 81.18 |
| JBD411 + JBD424 | 28.1 | 27.12 |
| JBD425 | 87.7 | 84.65 |
| JBD411 + JBD425 | 84.1 | 81.18 |
| JBD426 | 31.9 | 30.79 |
| JBD411 + JBD426 | 9.4 | 9.07 |
| JBD427 | 37.1 | 35.81 |
| JBD411 + JBD427 | 49.1 | 47.39 |

In Table 2, L. coryniformis JBD411 strain was able to reduce ammonia levels to 27% of the control. In the symbiotic pair groups of [JBD411+JBD421], [JBD411+JBD422], and [JBD411+JBD426], however, the ammonia levels were reduced to 3.19%, 9.17%, and 9.07% of the control respectively, demonstrating greater abilities of ammonia removal in the symbiotic pair groups than in the L. coryniformis JBD411.

TABLE 3

|  | ammonia conc. (mM) | % of control |
|---|---|---|
| control MRS | 103.6 | 100.0 |
| JBD410 | 33.2 | 32.0 |
| JBD421 | 29.7 | 28.7 |
| JBD410 + JBD421 | 20 | 19.3 |
| JBD422 | 36.4 | 35.1 |
| JBD410 + JBD422 | 13.3 | 12.8 |
| JBD423 | 22.3 | 21.5 |
| JBD410 + JBD423 | 44.2 | 42.7 |
| JBD424 | 84.1 | 81.2 |
| JBD410 + JBD424 | 17.9 | 17.3 |
| JBD425 | 87.7 | 84.7 |
| JBD410 + JBD425 | 32.4 | 31.3 |
| JBD426 | 31.9 | 30.8 |
| JBD410 + JBD426 | 15.8 | 15.3 |
| JBD427 | 37.1 | 35.8 |
| JBD410 + JBD427* | 12.5 | 12.1 |

In Table 3, L. acidophilus JBD410 strain was able to reduce ammonia to 32% of the control. In the symbiotic pair groups of [JBD410+JBD422] and [JBD410+JBD427], however, the ammonia levels were reduced to 12.8%, and 12.1% of the control respectively, demonstrating greater abilities of ammonia removal in the symbiotic pair groups than in the L. acidophilus JBD410.

TABLE 4

|  | ammonia conc. (mM) | % of control |
|---|---|---|
| control MRS | 103.6 | 100 |
| JBD401 | 39.4 | 38.03 |
| JBD421 | 29.7 | 28.67 |
| JBD401 + JBD421* | 8.5 | 8.20 |
| JBD422 | 36.4 | 35.14 |
| JBD401 + JBD422 | 14.7 | 14.19 |
| JBD423 | 22.3 | 21.53 |
| JBD401 + JBD423 | 50.4 | 48.65 |
| JBD424 | 84.1 | 81.18 |
| JBD401 + JBD424 | 9.8 | 9.46 |
| JBD425 | 87.7 | 84.65 |
| JBD401 + JBD425 | 72.3 | 69.79 |

TABLE 4-continued

| | ammonia conc. (mM) | % of control |
|---|---|---|
| JBD426 | 31.9 | 30.79 |
| JBD401 + JBD426 | 28.9 | 27.9 |
| JBD427 | 37.1 | 35.81 |
| JBD401 + JBD427 | 34.2 | 33.01 |

In Table 4, *L. amylovorus* JBD401 strain was able to reduce ammonia to 38% of the control. In the symbiotic pair groups of [JBD401+JBD421], [JBD401+JBD422], and [JBD401+JBD424, however, the ammonia levels were reduced to 8.2%, 14.19%, and 9.46% of the control respectively, demonstrating greater abilities of ammonia removal in the symbiotic pair groups than in the *L. amylovorus* JBD401.

TABLE 5

| | ammonia conc. (mM) | % of control |
|---|---|---|
| control MRS | 103.6 | 100 |
| JBD301 | 27.2 | 26.25 |
| JBD421 | 29.7 | 28.67 |
| JBD301 + JBD421 | 17.4 | 16.80 |
| JBD422 | 36.4 | 35.14 |
| JBD301 + JBD422* | 8.5 | 8.25 |
| JBD423 | 22.3 | 21.53 |
| JBD301 + JBD423 | 20.1 | 19.45 |
| JBD424 | 84.1 | 81.18 |
| JBD301 + JBD424 | 42.0 | 40.54 |
| JBD425 | 87.7 | 84.65 |
| JBD301 + JBD425 | 37.9 | 36.58 |
| JBD426 | 31.9 | 30.79 |
| JBD301 + JBD426 | 27.3 | 26.35 |
| JBD427 | 37.1 | 35.81 |
| JBD301 + JBD427 | 22.8 | 22.01 |

In Table 5, *L. reuteri* JBD301 strain was able to reduce ammonia to 26% of the control. In the symbiotic pair groups of [JBD301+JBD421], [JBD301+JBD422], [JBD301+JBD423], however, the ammonia levels were reduced to 16.8%, 8.25%, and 19.45% of the control respectively, demonstrating greater abilities of ammonia removal in the symbiotic pair groups than in the *L. reuteri* JBD301.

Through the continued throughput screening of the strains in the JINIS Co and Gut Microbiota Bank, we further discovered *Lactobacillus* strains and their symbiotic partner *Streptococcus* strains with ammonia removal ability as excellent as the previously identified JBD strains. These strains and symbiotic pair groups were also tested for ammonia removal ability as described in this invention.

TABLE 6

| Classification | Ammonia (% of control) | NH$_4$ reduction |
|---|---|---|
| control MRS | 100 | – |
| *L. reuteri* JBD400 | 35.4 | ++ |
| [*L. reuteri* JBD400 + *S. rubneri* JBD420] * | 11.6 | +++++ |
| *L. plantarum* JBD402 | 37.8 | ++ |
| [*L. plantarum* JBD402 + *S. lutetiensis* JBD421] | 26.7 | +++ |
| *L. rhamnosus* JBD406 | 40.5 | ++ |
| [*L. rhamnosus* JBD406 + *S. rubneri* JBD420] | 18.0 | +++++ |

In Table 6, *L. reuteri* JBD400, *L. plantarum* JBD402, and *L. rhamnosus* JBD406 were able to reduce ammonia to 35%, 37%, and 40% of the control group, respectively. In the symbiotic pair groups of [JBD400+JBD420], [JBD402+JBD421], [JBD406+JBD420], however, the ammonia levels were reduced to 11.6%, 26.7%, and 18.0% of the control, respectively, demonstrating greater abilities of ammonia removal in the symbiotic pair groups than in the pure culture.

Example 2. Identification and Deposit of Strains Having Ammonia Removal Ability

After identification of ammonia removal *Lactobacillus* strains in Experiment 1, precise 16S rRNA gene analysis was performed on them. Briefly, DNA was extracted from the anaerobic culture of each strain in the MRS medium, and 16s rDNA was amplified by PCR. PCR conditions were denaturation at 95° C. for 5 minutes and amplification of 30 times [95° C. for 30 seconds, 52° C. for 45 seconds, and 72° C. for 2 minutes] followed by incubation at 72° C. for 10 minutes. Universal primers (Sequence No. 1 and 2) shown below were used.

[Sequence No. 1]27 F:
5'-AGA GTT TGA TCC TGG CTC AG-3'

[Sequence No. 2]1492 R:
5'-GGT TAC CTT GTT ACG ACT T-3'

The obtained 16s rDNA sequences of the *Lactobacillus* strains were used for comparison with the database, including NCBI GenBank, DNA data bank of Japan, and European Nucleotide Archive. We confirmed *L. amylovorus* JBD401 (KACC 81052BP) and *L. coryniforrnis* JBD411 (KACC 81053BP) as novel species and deposited them in the Biological Resources Center in the Korean Agricultural Culture Collection (KACC) on Aug. 25, 2017.

After identification of ammonia removal *Streptococcus* strains in Example 1, precise 16S rRNA gene analysis was performed on them as described above. The obtained 16s rDNA sequences of the *Streptococcus* strains were used for comparison with the database, including NCBI GenBank, DNA data bank of Japan, and European Nucleotide Archive. We confirmed *S. lutetiensis* JBD421 strain (KACC 81054BP), *S. australis* JBD422 strain (KACC 81055BP), *S. mutans* JBD423 strain (KACC 81056BP), *S. vestibularis* JBD424 strain (KACC 81057BP), *S. sanguinis* JBD425 strain (KACC 81058BP), *S. parasanguinis* JBD426 strain (KACC 81059BP), and *S. gallinaceus* JBD427 strain (KACC 81060BP) as novel species and deposited them in the Biological Resources Center in the Korean Agricultural Culture Collection (KACC) on Nov. 30, 2017.

In addition, we confirmed *Lactobacillus reuteri* JBD400 (KACC 81122BP), *Lactobacillus plantarum* JBD402 (KACC 81121BP), *Lactobacillus rhamnosus* JBD406 (KACC 81123BP), and *S. lubneri* JBD420 (KACC 81124BP) as novel species and deposited them in the Biological Resources Center in the Korean Agricultural Culture Collection (KACC) on Jul. 7, 2020.

Example 3. In Vivo Evaluation of Neuroprotective Efficacy of the Strains with Ammonia Removal Ability An animal experiment was performed to evaluate the neuroprotective efficacy of candidate strains obtained through ammonia removal screening. To prepare microbial powder for animal testing, the candidate strains were cultured in MRS followed by centrifugation. The obtained cell pellet was freeze-dried after the addition of 10% skim milk powder and sugar.

All animal experiments were performed in accordance with the regulations of the Institutional Animal Care and Use Committee. Ten four-week-old male ICR mice were placed in a cage with food (10% fat; D12450B; Research Diets Inc, New Brunswick, NJ, USA) and water available ad libitum under a 12-h light/12-h dark cycle at 22° C. and 55%±5% humidity. After 1 week of acclimation, mice were randomly divided into with control or experimental group. Control mice were fed general feed while experimental mice fed ammonia-removing strains at $1\times10^7$ CFU/day for 7 days, either as pure culture powder or a symbiotic pair group as indicated. On the last day, hyperammonemia was induced by the injection of $^{15}NH_4Cl$ into the tail vein of the mice at a dose of 100 mg/kg. After 1 hour, blood was collected and the brain was isolated. After centrifugation of blood, the supernatant was collected for determination of ammonia concentration. The results are shown in Table 7 and FIG. 3.

TABLE 7

| No | Strain | Ammonia in blood (µg/ml) | % of Control |
|----|--------|--------------------------|--------------|
| 1 | Control | 5.32 ± 0.97 | 100.0 |
| 2 | JBD301 | 2.69 ± 1.06 | 50.6 |
| 3 | JBD301 + JBD421 | 0.88 ± 0.64 | 16.5* |
| 4 | JBD301 + JBD422 | 0.79 ± 0.72 | 14.8* |
| 5 | JBD401 | 2.91 ± 0.59 | 54.7 |
| 6 | JBD401 + JBD421 | 0.75 ± 0.25 | 14.1* |
| 7 | JBD401 + JBD424 | 0.43 ± 0.24 | 8.1* |
| 8 | JBD410 | 2.49 ± 0.34 | 46.8 |
| 9 | JBD410 + JBD421 | 1.27 ± 0.32 | 23.9 |
| 10 | JBD410 + JBD424 | 1.19 ± 0.42 | 22.4 |
| 11 | JBD411 | 2.26 ± 0.32 | 42.5 |
| 12 | JBD411 + JBD421 | 0.37 ± 0.11 | 7.0* |
| 13 | JBD411 + JBD424 | 0.84 ± 0.46 | 15.8 |

Figure 3:
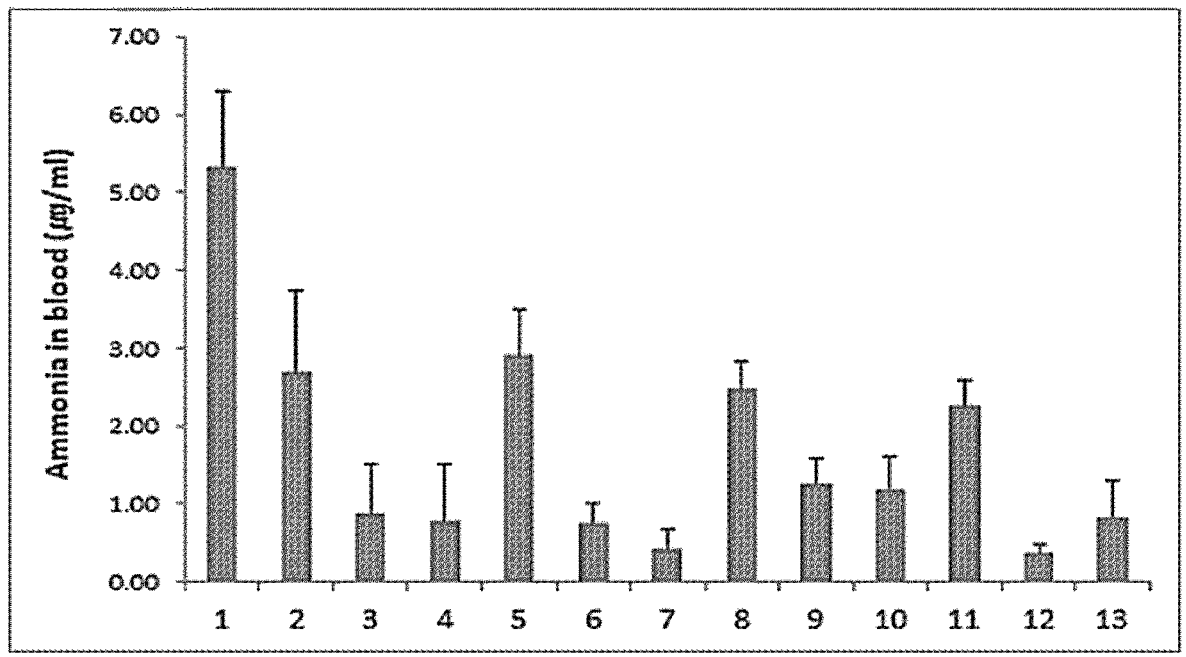
FIG. 3 presents the concentration of blood ammonia after inducing hyperammonemia in animals that administered the microbial strain or symbiotic pair microbes identified from the screening according to Example 1 (1: Control, 2: JBD301, 3: JBD301+JBD421, 4: JBD301+JBD422, 5: JBD401, 6: JBD401+JBD421, 7: JBD401+JBD424, 8: JBD410, 9: JBD410+JBD421, 10: JBD410+JBD424, 11: JBD411, 12: JBD411+JBD421, 13: JBD411+JBD424).

As shown in Table 7 and FIG. 3, the blood ammonia levels of mice fed the *Lactobacillus* JBD301, *Lactobacillus* JBD401, *Lactobacillus* JBD410, or *Lactobacillus* JBD411 powder were reduced to a level of 42% to 50% of the control group. In an agreement with in vitro data, the blood ammonia levels of mice fed the symbiotic pair of *Lactobacillus/Streptococcus*, [JBD301+JBD421], [JBD301+JBD422], [JBD411+JBD421], and [JBD401+JBD424] groups, were reduced to a level of 7%~16.5% of the control group, demonstrating greater abilities of ammonia removal in the symbiotic pair groups than in the pure culture group.

Also, the separated brain was crushed and centrifuged to collect the supernatant. The quantitative analysis of ammonia in the brain tissue is shown in Table 8 and FIG. 4.

TABLE 8

| No | Strain | Ammonia in brain (µg/g) | % of Control |
|----|--------|-------------------------|--------------|
| 1 | Control | 2.65 ± 0.56 | 100.0 |
| 2 | JBD301 | 1.35 ± 0.33 | 50.9 |
| 3 | JBD301 + JBD421 | 0.64 ± 0.46 | 24.2 |
| 4 | JBD301 + JBD422 | 0.26 ± 0.47 | 9.8* |
| 5 | JBD401 | 1.00 ± 0.46 | 37.7 |
| 6 | JBD401 + JBD421 | 0.42 ± 0.23 | 15.8 |
| 7 | JBD401 + JBD424 | 0.38 ± 0.24 | 14.3* |
| 8 | JBD410 | 1.74 ± 0.63 | 65.7 |
| 9 | JBD410 + JBD421 | 0.43 ± 0.19 | 18.1* |
| 10 | JBD410 + JBD424 | 1.05 ± 0.64 | 39.6 |
| 11 | JBD411 | 1.55 ± 0.20 | 58.5 |
| 12 | JBD411 + JBD421 | 0.22 ± 0.18 | 8.3* |
| 13 | JBD411 + JBD424 | 0.65 ± 0.54 | 24.5 |

Figure 4:
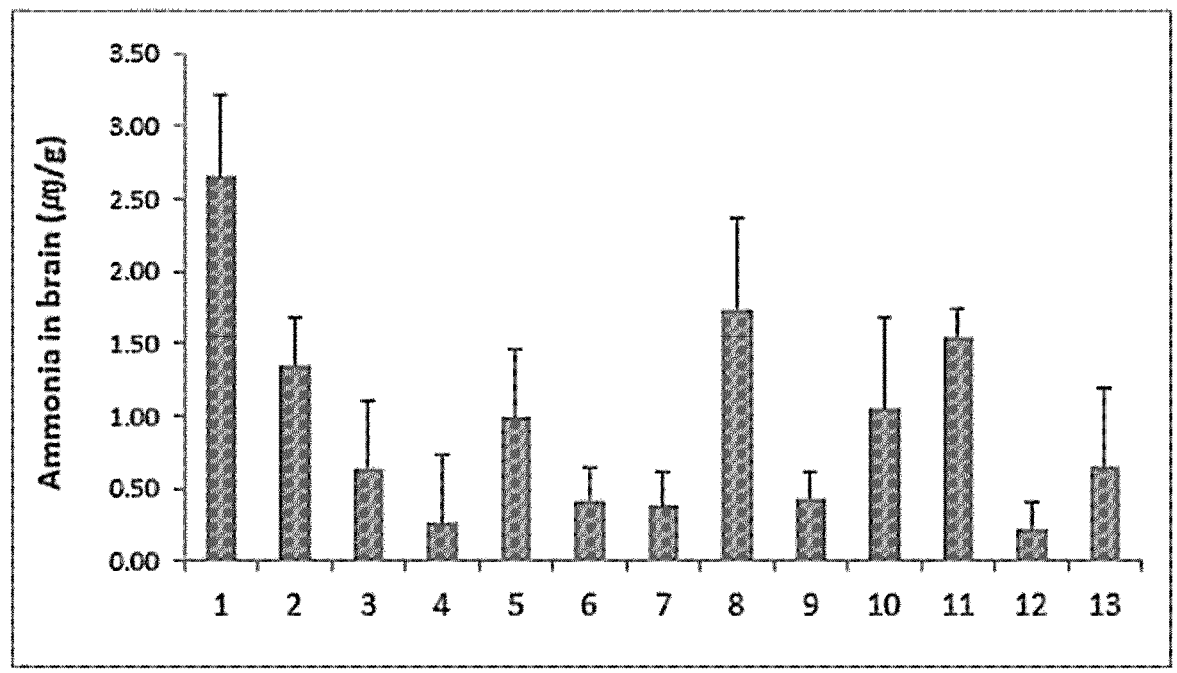
FIG. 4 presents the concentration of ammonia in brain tissue after inducing hyperammonemia in animals that administered the microbial strain or symbiotic pair microbes identified from the screening according to Example 1 (1: Control, 2: JBD301, 3: JBD301+JBD421, 4: JBD301+JBD422, 5: JBD401, 6: JBD401+JBD421, 7: JBD401+JBD424, 8: JBD410, 9: JBD410+JBD421, 10: JBD410+JBD424, 11: JBD411, 12: JBD411+JBD421, 13: JBD411+JBD424).

As shown in Table 8 and FIG. 4, the brain ammonia levels of mice fed the *Lactobacillus* JBD301, *Lactobacillus* JBD401, *Lactobacillus* JBD410, or *Lactobacillus* JBD411 powder were reduced to a level of 16% to 65% of the control group. In an agreement with blood data, the brain ammonia levels of mice fed the symbiotic pair of *Lactobacillus/Streptococcus*, [JBD301+JBD422], [JBD401+JBD424], [JBD410+JBD421], [JBD411+JBD421] groups, were reduced to a level of 8.3%~18.1% of the control group, demonstrating greater abilities of ammonia removal in the symbiotic pair groups than in the pure culture group.

Figure 5A:
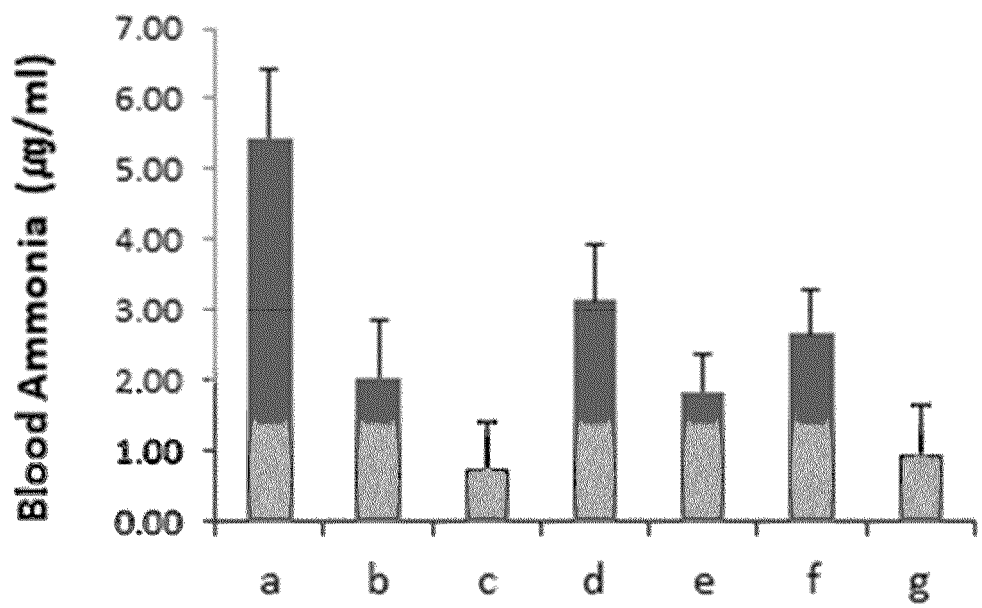
FIGS. 5A-5B present the concentration of ammonia in the blood in FIG. 5A and in the brain tissue in FIG. 5B after inducing hyperammonemia in animals that administered the microbial strain or symbiotic pair microbes identified from the screening according to Example 1 (a: Control, b: JBD400, c: JBD400+JBD420, d: JBD402, e: JBD402+JBD421, f: JBD406, g: JBD406+JBD420).
Figure 5B:
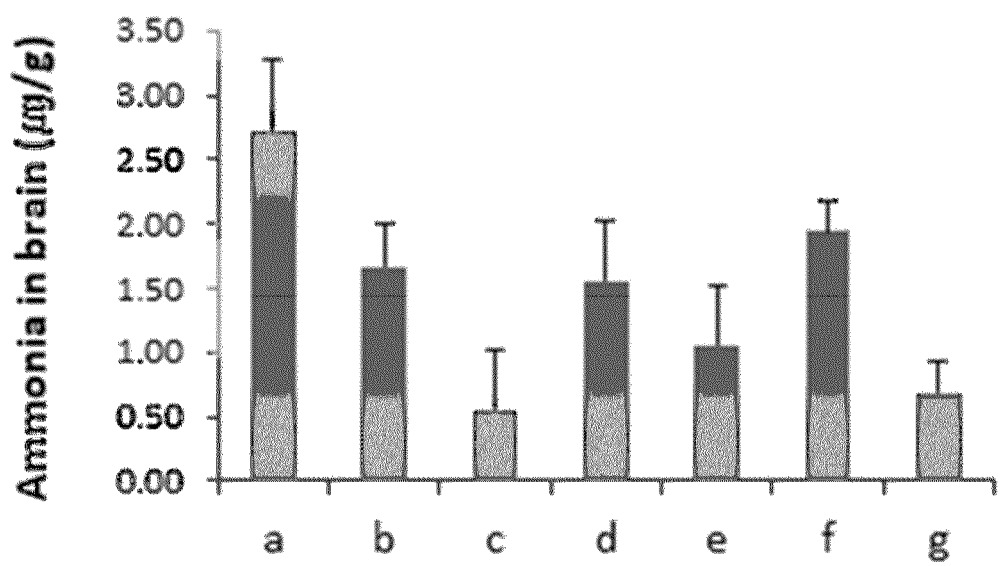

In addition, *Lactobacillus* strains and their symbiotic partner *Streptococcus* strains from the continued screen, *Lactobacillus* JBD400, *Lactobacillus* JBD402, *Lactobacillus* JBD406, *Streptococcus* JBD420, and *Streptococcus* JBD421 strains, were also tested for in vivo neuroprotective efficacy as described in this invention. The measurement results of ammonia in blood and brain tissue are shown in FIGS. 5A-5B. In agreement with previous data, it demonstrated consistently greater abilities of ammonia removal in the symbiotic pair groups of the *Lactobacillus/Streptococcus* than in the pure culture group. In particular, it was confirmed that ammonia in blood and brain tissue was reduced by more than 80% compared to the control group in the best symbiotic pair of the [JBD400+JBD420] group.

Figure 6A:
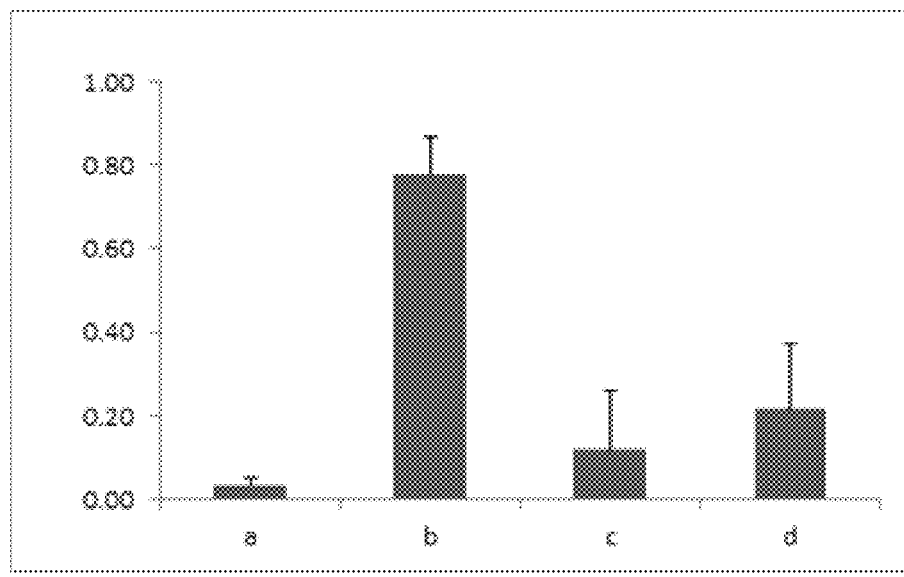
FIG. 6A presents the degree of neuronal cell death by measuring the caspase-9/DAPI staining ratio in brain tissues after hyperammonemia was induced in animals fed [JBD411+JBD421] and [JBD301+JBD422] according to the present invention.
Figure 6B:
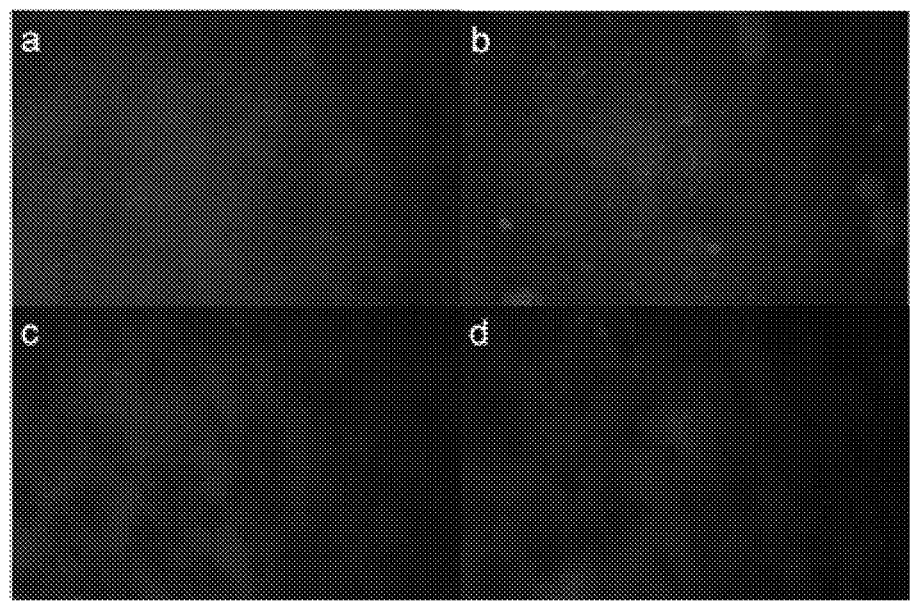
FIG. 6B presents the representative image of neuronal cell death by caspase-9/DAPI staining of brain tissues after hyperammonemia was induced in animals fed [JBD411+JBD421] and [JBD301+JBD422] according to the present invention.

For image analysis of the neuroprotective ability of the ammonia removal strain, brain tissue sections were prepared using a cryotome (Thermo Scientific), stained with DAPI, analyzed with a caspase kit (FLICA™, Fluorescent-Labeled Inhibitor of Caspases), and analyzed with a fluorescence microscope (Nikon). Representative images of the observed results are shown in Table 9 and FIGS. 6A-6B.

TABLE 9

| | | Caspase 9-stain/DAPI stain | |
|---|---|---|---|
| No | Strain | Mean | % HA Control |
| 1 | Control | 0.0371 | 5.06 |
| 2 | Hyperammonemia (HA) | 0.7325 | 100.00 |
| 3 | HA + [JBD411 + JBD421] | 0.1196 | 16.32 |
| 4 | HA + [JBD301 + JBD422] | 0.2158 | 29.46 |

As in Table 9 and FIG. 6, compared to the normal control group (a), the ratio of caspase 9-stained cells over DAPI-stained normal cells was significantly increased in the hyperammonemia group (b), indicating apoptosis due to ammonia neurotoxicity. In contrast, in the experimental group (c) fed [JBD411+JBD421], the ratio of caspase 9-stained cells over DAPI-stained normal cells was significantly reduced by more than 80%, being 16% of the hyperammonemia control. In the experimental group (d) fed [JBD301+JBD422], the ratio of caspase 9-stained cells over normal cells was reduced by more than 70%, being 29% of the hyperammonemia control.

Therefore, it was confirmed that the ammonia removal strains of the present invention can reduce ammonia in the body of a mammal and thus can prevent or treat hyperammonemia. It was also confirmed that the ammonia removal strains of the present invention are neuroprotective and thus can be usefully used for the prevention and treatment of neurological diseases.

Industrial Applicability

The ammonia removal strains and the composition in the present invention have a neuroprotective effect by their excellent ability to remove neurotoxic ammonia, and thus can be widely used as a preventive or therapeutic agent for hyperammonemia and neurological diseases caused thereby.

The invention claimed is:

1. *Lactobacillus* sp. and *Streptococcus* sp. pair having neuroprotective efficacy by lowering blood ammonia levels in mammals, and said *Lactobacillus* sp. and *Streptococcus* sp. pair being selected from the groups that include JBD301+JBD421, JBD301+JBD422, JBD301+JBD423, JBD400+JBD420, JBD401+JBD421, JBD401+JBD422, JBD401+JBD424, JBD402+JBD421, JBD406+JBD420, JBD410+JBD421, JBD410+JBD422, JBD410+JBD427, JBD411+JBD421, JBD411+JBD422, JBD411+JBD424, or JBD411+JBD426, wherein:

JBD301 is *Lactobacillus reuteri* JBD301 (KCTC 12606BP),
JBD400 is *Lactobacillus reuteri* JBD400 (KACC 81122BP),
JBD401 is *Lactobacillus* amylovorus JBD401 (KACC 81052BP),
JBD402 is *Lactobacillus plantarum* JBD402 (KACC 81121BP),
JBD406 is *Lactobacillus rhamnosus* JBD406 (KACC 81123BP),
JBD410 is *Lactobacillus acidophilus* JBD410 (KCTC 11515BP),
JBD411 is *Lactobacillus coryniformis* JBD411 (KACC 81053BP)
JBD420 is *Streptococcus lubneri* JBD420 (KACC 81124BP),
JBD421 is *Streptococcus lutetiensis* JBD421 (KACC 81054BP),
JBD422 is *Streptococcus australis* JBD422 (KACC 81055BP),
JBD423 is *Streptococcus mutans* JBD423 (KACC 81056BP),
JBD424 is *Streptococcus vestibularis* JBD424 (KACC 81057BP),
JBD426 is *Streptococcus parasanguinis* JBD426 (KACC 81059BP), and
JBD427 is *Streptococcus gallinaceus* JBD427 (KACC 81060BP).

2. A neuroprotective composition containing at least one of the *Lactobacillus* sp. and *Streptococcus* sp. pair of claim 1 as active ingredients.

3. A neuroprotective composition of claim 2, wherein said neuroprotective composition is characterized for its efficacy to prevent or treat hyperammonemia or to treat neurological diseases caused by hyperammonemia.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: universal primer 1

<400> SEQUENCE: 1
agagtttgat cctggctcag                                               20

<210> SEQ ID NO 2
<211> LENGTH: 19
<212> TYPE: DNA
<213> ORGANISM: Artificial Sequence
<220> FEATURE:
<223> OTHER INFORMATION: universal primer 2

<400> SEQUENCE: 2
ggttaccttg ttacgactt                                                19